(12) United States Patent
Shekhar et al.

(10) Patent No.: US 11,433,386 B2
(45) Date of Patent: Sep. 6, 2022

(54) ACTIVATION OF LOW METAL CONTENT CATALYST

(71) Applicant: ExxonMobil Chemical Patents Inc., Baytown, TX (US)

(72) Inventors: Mayank Shekhar, Houston, TX (US); Paul Podsiadlo, Humble, TX (US); Michel Molinier, Houston, TX (US); Scott J. Weigel, Allentown, PA (US); Travis D. Sparks, Deer Park, TX (US); Jocelyn A. Gilcrest, Mullica Hill, NJ (US); Joseph E. Gatt, Annandale, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 346 days.

(21) Appl. No.: 16/742,566

(22) Filed: Jan. 14, 2020

(65) Prior Publication Data

US 2020/0238271 A1 Jul. 30, 2020

Related U.S. Application Data

(60) Provisional application No. 62/796,926, filed on Jan. 25, 2019.

(51) Int. Cl.
*B01J 38/12* (2006.01)
*B01J 38/10* (2006.01)
(Continued)

(52) U.S. Cl.
CPC ............... *B01J 38/12* (2013.01); *B01J 6/001* (2013.01); *B01J 29/40* (2013.01); *B01J 29/7269* (2013.01);
(Continued)

(58) Field of Classification Search
CPC . B01J 6/001; B01J 29/068; B01J 29/40; B01J 29/7269; B01J 29/7276;
(Continued)

(56) References Cited

U.S. PATENT DOCUMENTS

| 5,939,220 A * | 8/1999 | Gunner | B01J 23/8993 420/466 |
| 9,868,117 B2 | 1/2018 | Detjen et al. | |

(Continued)

*Primary Examiner* — Brian A McCaig

(57) ABSTRACT

Methods are provided for activation of catalysts comprising low amounts of a hydrogenation metal, such as low amounts of a Group 8-10 noble metal. The amount of hydrogenation metal on the catalyst can correspond to 0.5 wt % or less (with respect to the weight of the catalyst), or 0.1 wt % or less, or 0.05 wt % or less. Prior to loading a catalyst into a reactor, the corresponding catalyst precursor can be first activated in a hydrogen-containing atmosphere containing 1.0 vppm of CO or less. The thus first-activated catalyst can be transferred to a reactor with optional exposure to oxygen during the transfer, where it can be further activated using a hydrogen-containing atmosphere containing 3.0 vppm of CO or higher, to yield a twice-activated catalyst with high performance. The catalyst can be advantageously a transalkylation catalyst or an isomerization catalyst useful for converting aromatic hydrocarbons.

24 Claims, 11 Drawing Sheets

(51) Int. Cl.
*B01J 29/40* (2006.01)
*B01J 29/72* (2006.01)
*B01J 6/00* (2006.01)
*C07C 5/22* (2006.01)
*C07C 6/06* (2006.01)
*B01J 37/00* (2006.01)
*B01J 37/20* (2006.01)
*B01J 37/02* (2006.01)
*C07C 15/08* (2006.01)

(52) U.S. Cl.
CPC ....... *B01J 29/7276* (2013.01); *B01J 37/0009* (2013.01); *B01J 37/0236* (2013.01); *B01J 37/20* (2013.01); *B01J 38/10* (2013.01); *C07C 5/222* (2013.01); *C07C 6/06* (2013.01); *C07C 15/08* (2013.01)

(58) Field of Classification Search
CPC .... B01J 37/0009; B01J 37/0236; B01J 37/14; B01J 37/16; B01J 37/20; B01J 38/10; B01J 38/12; C07C 5/222; C07C 5/2737; C07C 6/06; C07C 6/126; C07C 15/08; C07C 2529/068; Y02P 20/52
See application file for complete search history.

(56) References Cited

U.S. PATENT DOCUMENTS

| | | |
|---|---|---|
| 2005/0266979 A1 | 12/2005 | Boldingh et al. |
| 2006/0073965 A1 | 4/2006 | McCarthy et al. |
| 2008/0064588 A1 | 3/2008 | Boldingh et al. |
| 2011/0306686 A1* | 12/2011 | Jothimurugesan ... B01J 35/1019 518/715 |
| 2012/0330077 A1 | 12/2012 | Guillon et al. |
| 2015/0224493 A1 | 8/2015 | Kiss et al. |
| 2017/0072392 A1 | 3/2017 | Detjen et al. |
| 2019/0039055 A1 | 2/2019 | McCarthy et al. |
| 2019/0284056 A1* | 9/2019 | Elanany .................. B01J 29/44 |

* cited by examiner

ACTIVATION OF LOW METAL CONTENT CATALYST

PRIORITY

This application claims priority to U.S. Provisional Application No. 62/796,926, filed Jan. 25, 2019, the disclosures of which is incorporated in its entirety.

FIELD

Methods are provided for activation including initial reduction of low metal content catalysts, such as catalysts including low contents of precious metals. This disclosure is useful, e.g., in activating low metal-content catalysts used in aromatic hydrocarbon transalkylation and/or isomerization reactions.

BACKGROUND

Noble metal-containing catalysts are commonly used for a variety of purposes in refinery and chemical production environments. Applications for precious metal-containing catalysts can include hydroprocessing and various processes where saturation of aromatics and/or olefins is desirable.

Transalkylation is an example of a process where noble metal-containing catalysts are beneficial. During transalkylation, feeds including mixtures of $C_{9+}$ aromatics and toluene or benzene can be exposed to a catalyst including an appropriate zeolitic framework structure and a supported noble metal. The goal during a transalkylation process can be to transfer methyl groups from the $C_{9+}$ aromatics to toluene or benzene to form xylenes, while saturating olefins generated by dealkylation reactions and/or olefins generated by non-aromatics cracking reactions. During transalkylation, it can also be beneficial to reduce or minimize saturation of aromatic rings.

Many catalysts, such as transalkylation and isomerization catalysts, contain a molecular sieve and a hydrogenation metal such as a noble metal as the active ingredients. The manufacture of such catalysts usually involves a step of making a catalyst precursor comprising a mixture of the molecular sieve and the hydrogenation metal at a high oxidative state. After manufacture of a noble metal-containing catalyst precursor, such a catalyst precursor typically needs to be loaded into a reactor then activated before it can be put into normal operation to perform the intended catalytic function in the production of intended products. Typical activation procedures can include a reducing step for converting metal oxides present in the catalyst precursor to a lower oxidative state (e.g., an elemental state with a zero valency) using a hydrogen-containing atmosphere. Without proper activation, a catalyst may demonstrate less than desired activity or life.

U.S. Pat. No. 9,868,117 describes a method for improving a metal-impregnated catalyst, such as a catalyst impregnated with a noble metal. After loading a catalyst into a reactor, the reactor can be purged of CO in the presence of a hydrogen-containing atmosphere. This can allow for activation of the metal-impregnated catalyst while reducing or minimizing agglomeration of the metal.

There remains the need of improved activation methods for catalyst precursors comprising a molecular sieve and a hydrogenation metal.

SUMMARY

It has been found that the quality of reducing hydrogen atmosphere used in the activation step of the catalyst precursor comprising a molecular sieve and a hydrogenation metal can significantly impact the performance of the activated catalyst including but not limited to its catalytic activity and useful life. Particularly, the presence of certain gas, such as carbon monoxide (CO), in the hydrogen atmosphere at a high concentration such as 10 vppm or higher, can drastically affect the activity and/or life of the activated catalyst, especially if the catalyst precursor comprises a low concentration of the hydrogenation metal, e.g., ≤0.5 wt %, or ≤0.1 wt %, or ≤0.05 wt %, on the basis of the total weight of the catalyst precursor. It has been discovered that by reducing such catalyst precursor first in the presence of a first hydrogen-containing atmosphere comprising very low concentration of CO, e.g., at ≤1 vppm, either ex-situ or in-situ in a reactor, such reduced catalyst can be further activated in-situ in a reactor by using a second hydrogen-containing atmosphere having CO at a high concentration, e.g., at ≥10 vppm, to obtain a twice-activated catalyst with a high performance, notwithstanding the high CO concentration in the second hydrogen-containing atmosphere.

In various aspects of this disclosure, methods are provided for activation of catalysts containing low amounts of a hydrogenation metal, such as low amounts of a Group 8-10 noble metal. Prior to loading a low metal catalyst into a reactor, the corresponding catalyst precursor can be activated in a hydrogen-containing atmosphere containing 1.0 vppm of CO or less. This can reduce or minimize detrimental effects associated with CO exposure prior to initial reduction, such as metal aggregation and/or other catalyst deactivation. After the initial reduction, the catalyst can maintain activity after exposure to higher levels of CO. Additionally or alternately, the catalyst can maintain activity after exposure to an oxygen-containing environment and a subsequent additional reduction step.

DETAILED DESCRIPTION

Overview

Figure 1:
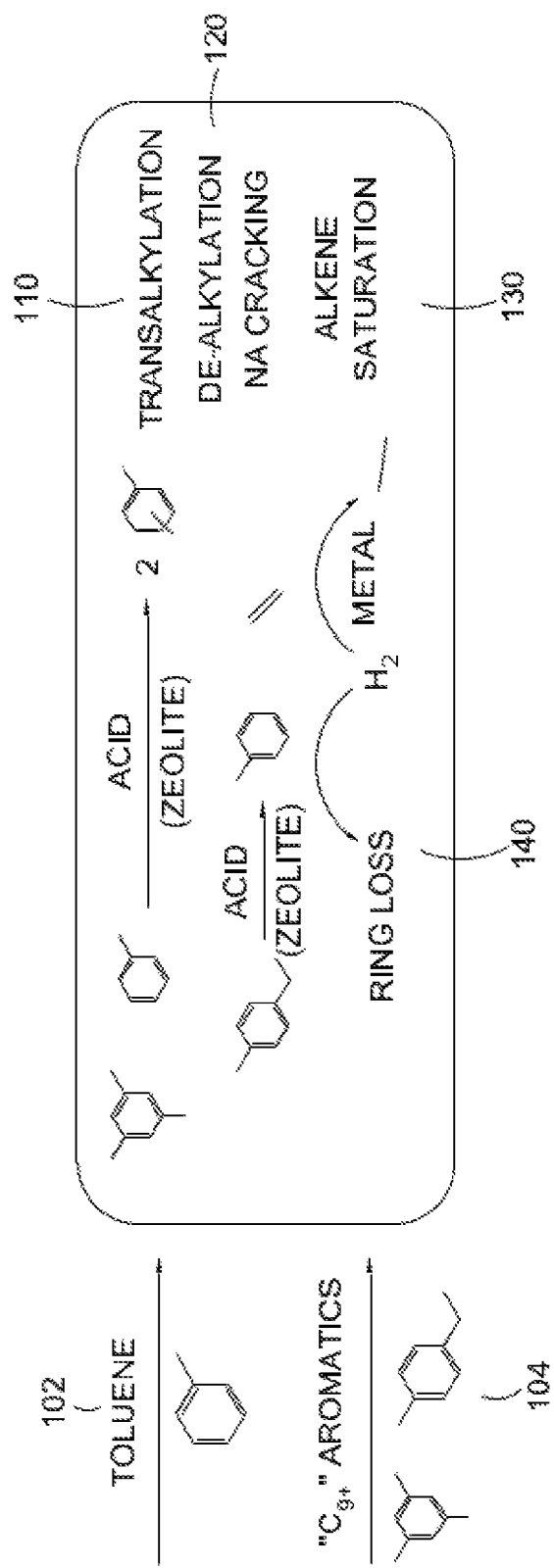
FIG. 1 schematically shows exemplary chemical reactions that can occur during a transalkylation process.

In this disclosure, a method is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a metal" include embodiments where one, two or more metals are used, unless specified to the contrary or the context clearly indicates that only one metal is used.

As used herein, "vppm" means parts per million by volume, "v %" means percent by volume, "wppm" means parts per million by weight, and "wt %" means percent by weight.

In this disclosure, a "catalyst precursor" refers to a catalyst composition that may be subject to a step of activation before it is put into intended operation to perform the desired level of intended catalytic function.

As used herein, a "molecular sieve" is a natural or an artificial material having pores with regular structure and/or shape, and a "zeolite" is type of molecular sieve having a porous framework structure built from tetrahedra atoms connected by bridging oxygen atoms. Examples of known zeolite frameworks are given in the "Atlas of Zeolite Frameworks" published on behalf of the Structure Commission of the International Zeolite Association", 6th revised edition, Ch. Baerlocher, L. B. McCusker, D. H. Olson, eds., Elsevier, New York (2007) and the corresponding web site, http://www.iza-structure.org/databases/. Under this definition, a zeolite can refer to aluminosilicates having a zeolitic framework type as well as crystalline structures containing oxides of heteroatoms different from silicon and aluminum. Such heteroatoms can include any heteroatom generally known to be suitable for inclusion in a zeolitic framework, such as gallium, boron, germanium, phosphorus, zinc, antimony, tin, and/or other transition metals that can substitute for silicon and/or aluminum in a zeolitic framework.

For the purposes of this disclosure, nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6th Edition, by F. Albert Cotton et al. (John Wiley & Sons, Inc., 1999).

In various aspects, systems and methods are provided for activation of catalyst precursors containing low amounts of a hydrogenation metal, such as low amounts of a Group 8-10 noble metal. The amount of metal contained in (including but not limited to supported on any support, including but not limited to the molecular sieve and/or binder) the catalyst precursor can correspond to 0.5 wt % or less (with respect to the total weight of the catalyst), or 0.1 wt % or less, or 0.05 wt % or less. In this disclosure, the concentration of a metal in a catalyst precursor or a catalyst is calculated as the weight percentage of the mental relative to the total weight of the catalyst or catalyst precursor, regardless of the oxidative state of the metal and the specific chemical(s) in which the metal is present in. Thus, in a catalyst precursor consisting of a molecular sieve and $PtO_2$, the concentration of the metal Pt is calculated as the weight percent of element Pt relative to the total weight of the catalyst precursor.

A catalyst precursor comprising a molecular sieve and a metal such as noble metal can be fabricated by any of the traditional methods, including but not limited to incipient wetness impregnation, slurry impregnation, physical blending, and the like. In a preferred method, a liquid dispersion such as a solution, preferably an aqueous dispersion such as an aqueous solution, of a compound (e.g., a salt) of the metal is used to impregnate the solid molecular sieve to obtain a mixture, which is subsequently dried and/or calcined to obtain a catalyst precursor comprising the molecular sieve and the metal. The metal can be supported on the external surface of the molecular sieve particles, or enter into the pores and/or channels in the molecular sieve and attach to the internal surface thereof. The metal can be present in the form of inorganic or organic salt, complex, oxide, or other forms in any oxidative state in the catalyst precursor. For the metal to perform the desired catalytic function such as hydrogenation at the desired level, it is highly desirable that the metal is distributed on the external and/or internal surfaces in the catalyst in a scattered fashion instead of in agglomerated form. For catalysts with a low loading of metal, scattered distribution of the metal in the catalyst is even more important for a high activity of the metal component.

Prior to loading a catalyst into a reactor, the corresponding catalyst precursor can be activated in a hydrogen-containing atmosphere containing 1.0 vppm of CO or less, or 0.3 vppm of CO or less, such as a hydrogen-containing atmosphere including substantially no CO down to a detection limit. The activation can correspond to exposing the catalyst precursor to the hydrogen-containing atmosphere under conditions suitable for reducing at least a portion of the metal on the catalyst precursor. After activation, the catalyst can then be transported to and/or loaded into the reactor. While subsequent exposure to CO may temporarily reduce catalyst activity, the catalyst activity can return to baseline upon removal of the CO. Examples of low metal content catalysts can include xylene isomerization catalysts and transalkylation catalysts.

One of the difficulties with use of low metal content catalysts is that such catalysts have a greater susceptibility to deactivation if the corresponding catalyst precursor is reduced in the presence of CO. Without being bound by any particular theory, it is believed that CO can cause aggregation of metal particles. Additionally, it is believed that CO may cause further deactivation by other mechanism(s). For a conventional catalyst with a metal content of 1.0 wt % or more, such exposure to CO has only a minimal impact on reactivity. The activity loss, however, is more pronounced for low metal content catalysts, such as catalysts with a metal content of 0.5 wt % or less, or 0.1 wt % or less, or 0.05 wt % or less.

Due to the potential for substantial activity loss if a low metal content catalyst precursor is reduced in the presence of CO, various start-up procedures have been developed to avoid such activity loss, such as the procedures described in U.S. Pat. No. 9,868,117. While such procedures are effective, the procedures require reducing the low metal content catalyst in a hydrogen-containing environment that is substantially free of CO. Unfortunately, the hydrogen sources available in a refinery typically include a CO content of roughly 10 vppm or more. Thus, to implement a procedure such as the procedure described in U.S. Pat. No. 9,868,117 can potentially require bringing in a separate source of high purity hydrogen, which may not be readily available.

It has been discovered that the need to bring high purity hydrogen into a refinery or chemical plant setting can be avoided by instead reducing a low metal content catalyst precursor prior to transport of the catalyst and/or prior to loading of the catalyst into the reactor. This can allow the initial reducing to be performed in any convenient reaction vessel, such as a reaction vessel with access to a convenient source of high-purity hydrogen. After the initial reduction, it has been discovered that low metal content catalyst can maintain activity after subsequent exposure to oxygen followed by subsequent reduction, even though CO may be present during the subsequent steps.

Catalyst activation (i.e., activation of a catalyst precursor corresponding to the catalyst) can refer to a variety of procedures that are performed after loading a catalyst into a reactor and prior to exposing the catalyst to a hydrocarbon or hydrocarbonaceous stream. Catalyst activation can typically include a heating and/or dry-out phase to increase the catalyst temperature to a temperature suitable for the next phase of activation, which may correspond to reducing the catalyst. Optionally, a catalyst can be sulfided after the reduction step.

In this discussion, the term "catalyst" is used to refer to both sulfided noble metal-containing catalysts as well as reduced noble metal-containing catalysts in compositional states prior to/other than sulfided. Prior to being reduced to form a catalyst, the hydrogenation metal supported on the zeolitic support can be referred to as a catalyst precursor.

Activation Conditions and Subsequent Reactor Loading

In various aspects, a low metal content catalyst can be activated by heating and reduction in the presence of an environment include 1.0 vppm of CO or less, or 0.1 vppm of CO or less, such as having substantially no CO. The reduction can be performed in the presence of a hydrogen-containing environment, while the heating can optionally be performed in the presence of either a hydrogen-containing environment or an inert gas environment.

A hydrogen-containing first atmosphere can correspond to an atmosphere that includes 1.0 vol % or more of $H_2$, or 3.0 vol % or more, or 5.0 vol % or more, or 10 vol % or more, such as up to an atmosphere including roughly 100 vol % hydrogen. The balance of the hydrogen-containing environment or the inert gas environment can correspond to an inert gas, such as $N_2$ or a noble gas (i.e., Ar, He, Ne). Optionally, $CO_2$ can be present, so long as the CO concentration is 1.0 vppm or less, or 0.3 vppm or less. Preferably, the atmosphere is substantially free of $H_2O$, such as containing 1000 vppm or less of $H_2O$, or 100 vppm or less, or 10 vppm or less. Preferably, the atmosphere can be substantially free of $O_2$, such as containing 1 vppm or less.

The atmosphere can be static, or a flow corresponding to the atmosphere composition can be introduced into the vessel containing the low metal content catalyst during at least a portion of the heating and/or reduction. The pressure during heating and/or reduction can be any convenient pressure, such as a pressure of 0.1 MPa-a to 5.0 MPa-a, or 0.1 MPa-a to 3.6 MPa-a. The heating step can be used to increase the temperature of the catalyst to a target temperature for reducing the catalyst. This temperature is typically selected based on the metal or metals to be reduced, but can correspond to a temperature of 150° C. to 500° C., or 150° C. to 420° C., or 200° C. to 400° C., or 200° C. to 360° C. During reduction, the catalyst can be held at a desired temperature for a period of time in the presence of the hydrogen-containing atmosphere, such as a hold time of 0.5 hours to 10 hours. After reduction the catalyst can be at least partially cooled in the presence of a hydrogen-containing atmosphere or an inert atmosphere.

After reducing the metal on the catalyst, the reduced catalyst can optionally be exposed to an oxygen-containing third atmosphere for a period of time. An example of the third atmosphere is air. An atmosphere at least partially composed of air can have an $O_2$ concentration of 1.0 vol % to 20 vol %. The reduced catalyst can be exposed to the third atmosphere for a period of time. The exposure period can correspond to as little as a minute or a few minutes up to an exposure period of weeks, months, or years. An example of an exposure period for the third atmosphere can be a period of 0.5 hours to 1000 hours, or 0.5 hours to 250 hours. More generally, the exposure period can be any convenient time from 0.5 hours to up to a plurality of years or possibly more. One reason that the reduced catalyst may be exposed to an oxygen-containing third atmosphere is due to transport from the vessel where the reduction is performed to the reactor where the catalyst is loaded for performing a refinery or chemical plant process.

After transport and/or other exposure to a third atmosphere, the reduced catalyst can be loaded into a reactor. The catalyst loaded into the reactor can then be exposed to another reducing step. The reducing step can be similar to the reducing step described above, with the exception that the second atmosphere for the second reducing step can optionally include 5.0 vppm or more of CO. For example, the second atmosphere can include 5.0 vppm to 25 vppm of CO, or 5.0 vppm to 20 vppm.

Low Metal Content Catalysts

In this discussion, a metal-containing catalyst refers to a catalyst that includes one or more hydrogenation metals supported on a support material. Optionally but preferably, at least one of the one or more hydrogenation metals can correspond to a Group 8-10 noble metal. Examples of suitable Group 8-10 noble metals for use as a hydrogenation metal can include Pt, Pd, Ru, Ir, Os, Rh, or combinations thereof. More generally, the one or more hydrogenation metals can include Pt, Pd, Ru, Rh, Ir, Os, Ni, Re, Co, Fe, or a combination thereof. Optionally, the catalyst can include one or more additional metals from outside of Groups 8-10, such as any metal typically included in a xylene isomerization catalyst or a transalkylation catalyst. Examples of such additional metals can include Sn, Ag, Ga, Cu, Mo, and/or other metals that can form alloys with Pt. In some preferred aspects, the hydrogenation metal can be Pt. The amount of hydrogenation metal supported on the catalyst can be 0.001 wt % to 0.5 wt %, or 0.001 wt % to 0.1 wt %, or 0.001 wt % to 0.05 wt %.

Catalysts can be formulated without a separate binder or matrix material and/or can be optionally bound with a separate binder or matrix material prior to use. Binders can be resistant to temperatures of the use desired and are attrition resistant. Binders may be catalytically active or inactive and include other zeolites, other inorganic materials such as clays and metal oxides such as alumina, silica, silica-alumina, zirconia, yttria, titania, and combinations thereof. Clays may be kaolin, bentonite and montmorillonite and are commercially available. They may be blended with other materials such as silicates. Other binary porous matrix materials in addition to silica-alumina include materials such as silica-magnesia, silica-thoria, silica-zirconia, silica-beryllia and silica-titania. Ternary materials such as silica-alumina-magnesia, silica-alumina-thoria and silica-alumina-zirconia can also be suitable for use as binders. A zeolite can be combined with binder in any convenient manner. For example, a bound catalyst can be produced by starting with powders of both the zeolite and binder, combining and mulling the powders with added water to form a mixture, and then extruding the mixture to produce a bound catalyst of a desired size. Extrusion aids can also be used to modify the extrusion flow properties of the zeolite and binder mixture.

The amount of zeolite in a support including a binder can be from about 5 wt % zeolite to about 100 wt % zeolite relative to the combined weight of binder and zeolite. For example, the amount of zeolite can be about 30 wt % to about 100 wt %, or about 30 wt % to about 90 wt %, or about 30 wt % to about 80 wt %, or about 30 wt % to about 70 wt %, or about 50 wt % to about 100 wt %, or about 50 wt % to about 90 wt %, or about 50 wt % to about 80 wt %, or about 50 wt % to about 70 wt %, or about 60 wt % to about 90 wt %, or about 60 wt % to about 80 wt %, or about 60 wt % to about 70 wt %.

After combining a zeolite with any optional binder, the zeolite can be extruded to form support particles. Alternatively, support particles may be formed by any other convenient method. After forming support particles, the support particles can be impregnated with the base metal salts using an impregnation solution that also includes a dispersion agent. Additionally or alternately, the metals on the support can be introduced onto the support by any other convenient method for forming a supported catalyst. Examples of other types of methods for addition of metal to a catalyst precursor can include, but are not limited to, solution addition to an extrusion mix, ion exchange, vapor phase deposition, or any other convenient method.

Impregnation, such as impregnation by incipient wetness or ion exchange in solution, is a commonly used technique for introducing metals into a catalyst that includes a support. During impregnation, a support is exposed to a solution containing a salt of the metal for impregnation. There are many variables that can affect the dispersion of the metal salt during impregnation, including the concentration of the salt, the pH of the salt solution, the point of zero charge of the support material, but not excluding other variables that may also be important during incipient wetness or ion exchange impregnation. Multiple exposure steps can optionally be performed to achieve a desired metals loading on a catalyst. After impregnating a support with a metal salt, the support can optionally be dried to remove excess water. The drying can be performed under any convenient atmosphere, such as air, at a temperature from about 80° C. to about 200° C.

Examples of noble metal-containing catalysts that include one or more noble metals supported on an (optionally bound) zeolitic support can be xylene isomerization catalysts and transalkylation catalysts. Suitable types of zeolites for xylene isomerization or transalkylation catalysts can include medium pore zeolitic framework structures. Examples of suitable types of medium-pore zeolitic framework structures can include MFI (e.g., ZSM-5), MEL (e.g., ZSM-11), MTW, MWW (e.g., MCM-22, MCM-49, and MCM-56), and MOR (e.g., EMM-34).

TRANSALKYLATION EXAMPLES—STARTUP AND EXPOSURE CONDITIONS

Transalkylation is a process for conversion of $C_{9+}$ aromatics and $C_{6-7}$ aromatics (i.e., benzene and/or toluene) into xylenes ($C_8$ aromatics). This can allow for conversion of two lower value feeds into a product including an increased percentage of higher value xylenes.

FIG. 1 shows an overview of the desired reactions during transalkylation and an undesirable side reaction that can preferably be reduced or minimized. In the example shown in FIG. 1, toluene 102 and a mixture of $C_{9+}$ aromatics corresponding to a heavy aromatic reformate 104 correspond to the input feeds for transalkylation. 1,3,5-tri-methylbenzene and 1-ethyl-4-methylbenzene are shown as examples of components present in the heavy aromatic reformate 104, but it is understood that a variety of $C_{9+}$ compounds can be present. The desirable reactions during a transalkylation process correspond to transalkylation 110, dealkylation 120, and alkene saturation 130. Preferably, ring loss 140 occurs in a reduced or minimized amount.

In order to investigate the impact of various startup and exposure conditions on transalkylation catalysts, samples of catalyst precursors for a transalkylation catalyst including 0.03 wt % Pt supported on an alumina bound zeolite were exposed to four different types of reducing conditions. The first set of conditions corresponded to in-situ reduction using high purity hydrogen. The second set of conditions corresponded to in-situ reduction with a hydrogen stream including 10 vppm CO. The third set of conditions were selected to represent ex-situ reduction followed by a short exposure to an oxygen-containing atmosphere (e.g., air). The fourth set of conditions were selected to represent ex-situ reduction followed by a longer exposure to air relative to the third set of conditions. In the third and fourth set of conditions, an additional reducing step in an atmosphere including 10 vppm CO was performed after the exposure to the oxygen-containing atmosphere. "In-situ" means inside a reactor where the catalyst is loaded for eventually performing its normal intended use. "Ex-situ" means in an environment other than in a reactor where the catalyst is loaded for eventually performing its normal intended use.

The catalysts reduced using the four procedures were then evaluated for catalyst performance in transalkylation (TA) service using typical feeds for transalkylation. The transalkylation feeds corresponded to mixtures of tailed heavy aromatic reformate (a mixture primarily including various $C_{9+}$ aromatics) and toluene. Most of the tests were performed using 50 wt % tailed heavy aromatic reformate and 50 wt % toluene.

The catalyst performance was evaluated under the following conditions: a weight hourly space velocity (WHSV) of 3 $hr^{-1}$; a reactor pressure of 360 psig (~2.4 MPa gauge pressure); a molar ratio of $H_2$:to hydrocarbons in the feed of roughly 2.0; and an inlet temperature of 660° F. (~350° C.). For the performance evaluation, the reactor was loaded with 30 grams of transalkylation catalyst (loaded as whole extrudates) mixed with 30 grams of inert diluent particles. The transalkylation catalyst samples corresponded to the samples that had been exposed to flowing air for either 3 hours or 7 days, according to the procedures described above.

There are several ways to characterize the performance of the catalyst during a transalkylation reaction. One option is to characterize the total amount of conversion of $C_7$, $C_9$, and $C_{10}$ compounds in the feed into other components. A second option is to characterize the amount of xylenes produced as a result of the conversion of the $C_7$, $C_9$, and $C_{10}$ compounds. Still another option is to characterize the concentration of ethylbenzene in the products. Yet another option is to characterize the amount of removal of ethyl side chains from ethylated aromatic rings, which can also be referred to as de-ethylation. For conversion of $C_7$, $C_9$, and $C_{10}$ compounds, a desirable target can be to achieve 50% or more conversion. With regard to de-ethylation, a desirable target can be to have 90% de-ethylation or more. For ethylbenzene content in the products, a desirable target can be to have 0.4 wt % ethylbenzene or less.

Testing data are presented in the accompanying drawing FIGS. 2-21, which are described below. In these drawings, "ToS" means time on stream, "EB" mean ethylbenzene, "INLET" means inlet temperature, "AVG" means average temperature, "CONV." means conversion, "DE-C2" means de-ethylation, "ART" means average reactor temperature, and "10 PPM CO" means in a given time period, the feed to the reactor includes 10 vppm of CO.

Transalkylation Example 1—Baseline

The first set of conditions was designed to represent an in-situ reduction of catalyst in a reactor. After loading the catalyst precursor into the reactor, the reactor was pressurized to 2.4 MPa-g with $H_2$. $H_2$ was then flowed through the reactor at ~20° C. for 3 hours. The hydrogen treat gas corresponded to electrolytic hydrogen, so substantially no CO was included in the treat gas during initial reduction. The reactor temperature was then increased to ~350° C. using a heating ramp rate of roughly 40° C./hr. The temperature was maintained at ~350° C. for 2 hours. The catalyst was then sulfided by exposing the catalyst to 400 wppm $H_2S$ in $H_2$ for 1 hour. The hydrocarbon feed was then introduced into the reactor while maintaining the sulfiding gas flow for 1 hour. The gas source was then switched to 100% $H_2$. This startup procedure was intended to represent in-situ startup of a low metal content catalyst using a specialized hydrogen source.

Figure 2:
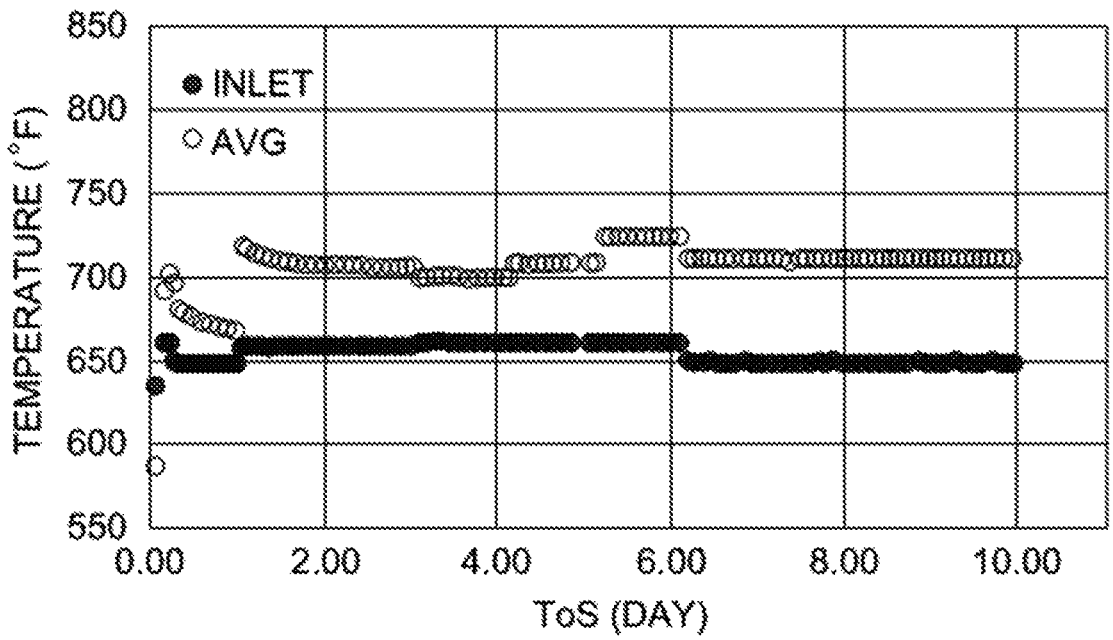
FIG. 2 shows temperatures associated with a first exemplary transalkylation process.
Figure 3:
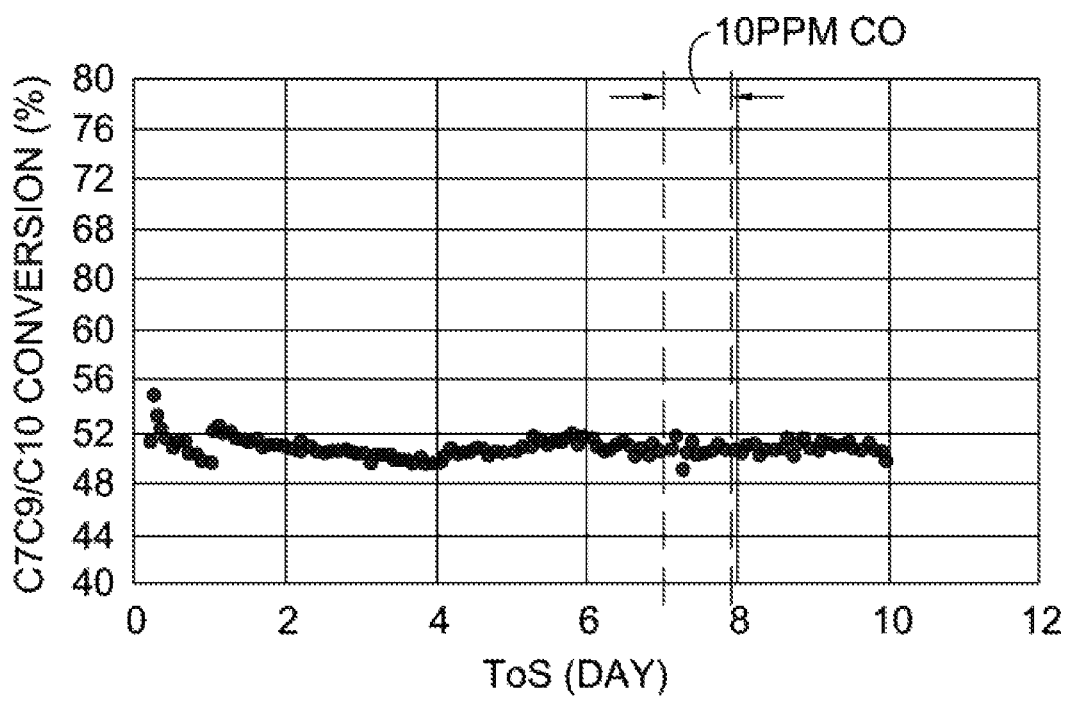
FIG. 3 shows $C_7$, $C_9$, and $C_{10}$ conversion for the transalkylation process of FIG. 2.

FIGS. 2-6 show details regarding the reaction conditions and results from performing the transalkylation process using the catalyst reduced according to the first procedure using the electrolytic hydrogen (i.e., substantially no CO in the hydrogen stream). The results in FIGS. 2-6 represent baseline results for performing an in-situ reduction, where the low metal content catalyst would not be exposed to oxygen after the reduction process. FIG. 2 shows the temperature profile at the reactor inlet and the average reactor temperature that was needed to maintain the stable levels of conversion of the toluene, $C_9$, and $C_{10}$ compounds in the feed (shown in FIG. 3). The target amount of conversion was 52%. As shown in the figures, the temperature profile in FIG. 2 that was required to maintain the stable conversion in FIG. 3 was relatively flat. However, a brief increase in temperature was required on day 7, due to introduction of 10 vppm CO into the reaction environment. The CO temporarily suppressed the activity of the transalkylation catalyst, but the activity returned on day 8 when the CO was removed from the reaction environment.

Figure 4:
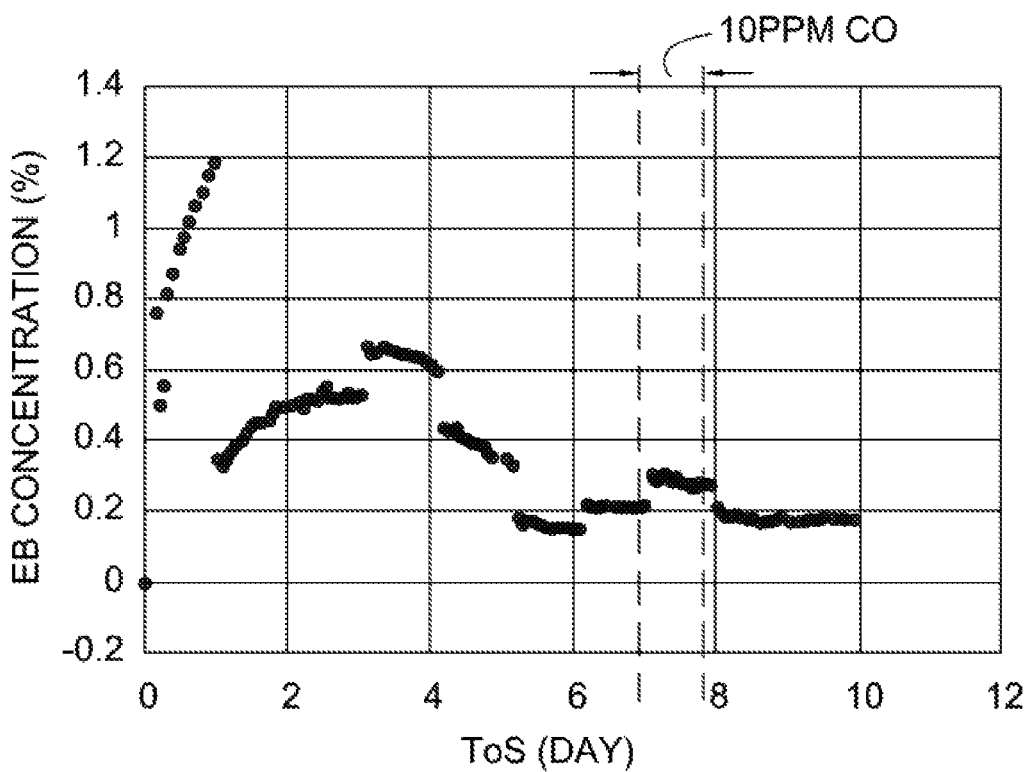
FIG. 4 shows ethylbenzene conversion for the transalkylation process shown in FIG. 2.

The ethylbenzene concentration in the reaction product is shown in FIG. 4, after an initial period, the ethylbenzene concentration also becomes relatively stable at stable temperature. Again, during the introduction of CO into the hydrogen treat gas on day 7, the amount of ethylbenzene in the products increased, but returned to the lower level when the CO was removed on day 8.

Figure 5:
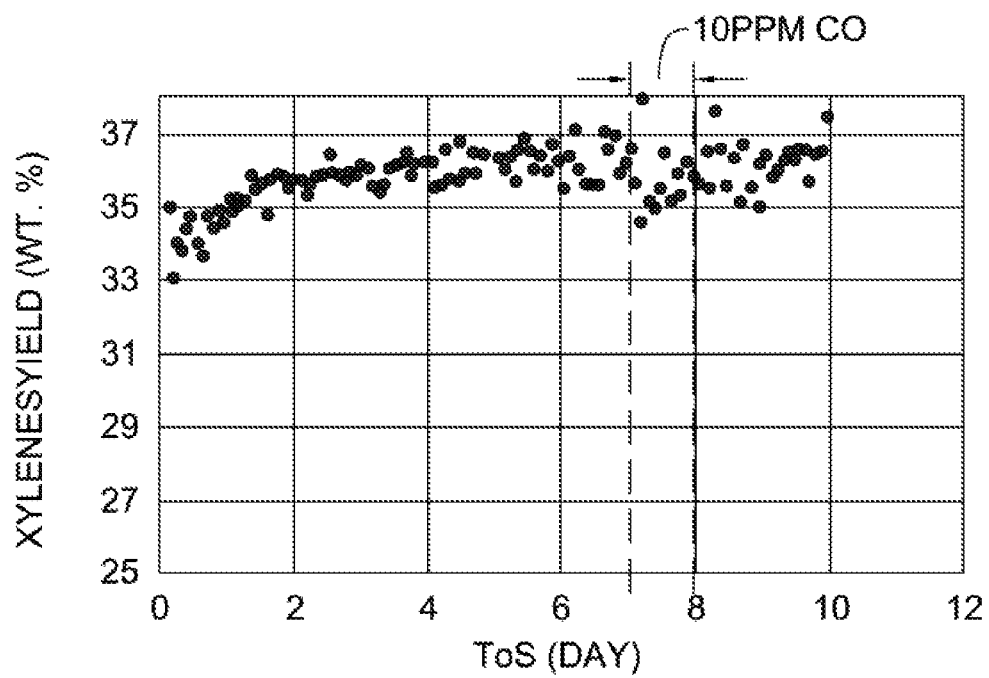
FIG. 5 shows xylene yield for the transalkylation process of FIG. 2.

FIG. 5 shows xylene yield from the transalkylation. After the initial period, the xylene yield is also relatively constant at constant temperature. The introduction of CO on day 7 may have reduced the xylene yield, but returning to pure hydrogen on day 8 removed any such loss in yield.

Figure 6:
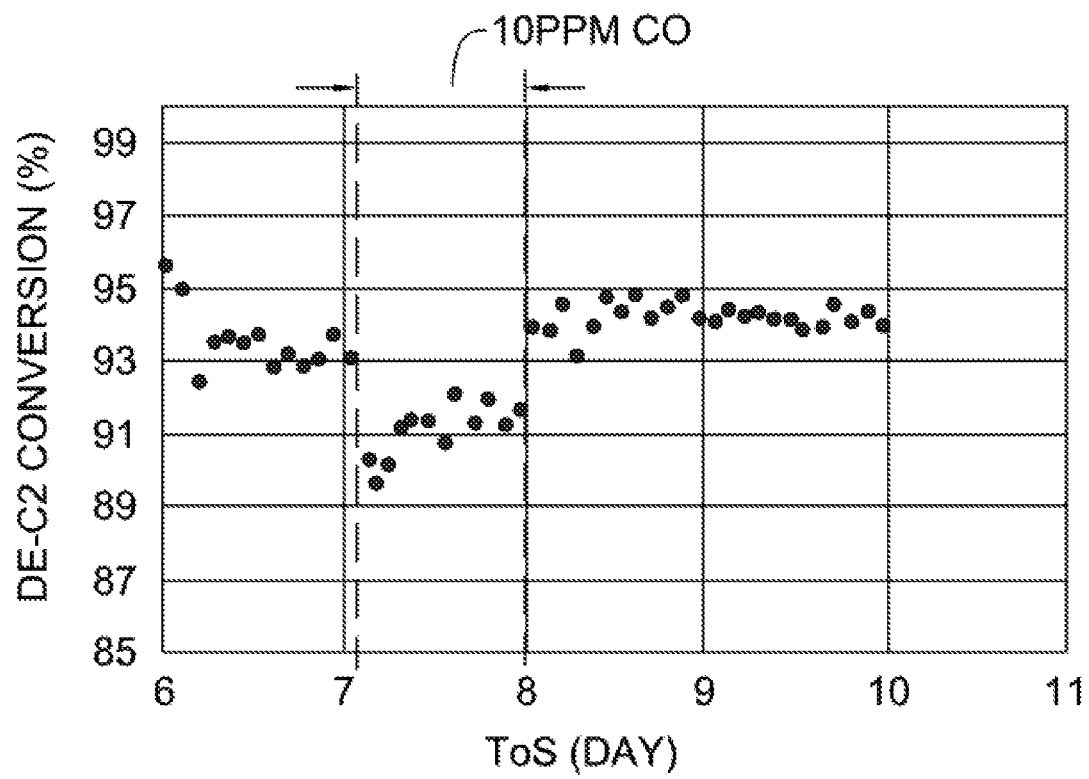
FIG. 6 shows de-ethylation conversion for the transalkylation process shown in FIG. 2.

FIG. 6 shows the amount of de-ethylation in the products. As shown in FIG. 6, the removal of ethyl groups from aromatic rings was stable with stable temperature, with the exception of day 7 when CO was added to the hydrogen. Similar to the other figures, the full activity for de-ethylation returned on day 8. It is noted that de-ethylation was greater than 90% both with and without the presence of CO in the hydrogen treat gas.

Transalkylation Example 2—Initial Reduction with 10 Vppm CO (Comparative)

A second set of reducing conditions was similar to the first set, but the hydrogen treat gas included 10 vppm of CO at all points during the startup procedure. This was selected to simulate using a hydrogen stream that would be expected to be available at a refinery or chemical plant site, such as a reformer hydrogen stream. After sulfidation, the hydrogen treat gas was switched to 100% hydrogen, in order to allow for comparison with the activity of the baseline startup procedure.

Figure 7:
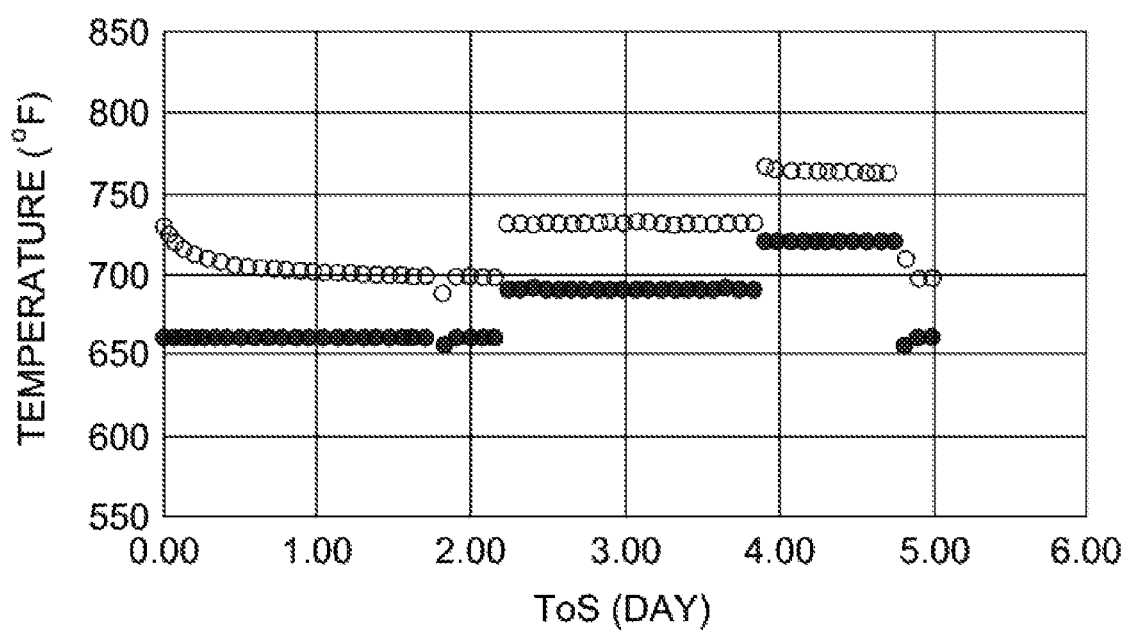
FIG. 7 shows temperatures associated with a second exemplary transalkylation process.
Figure 8:
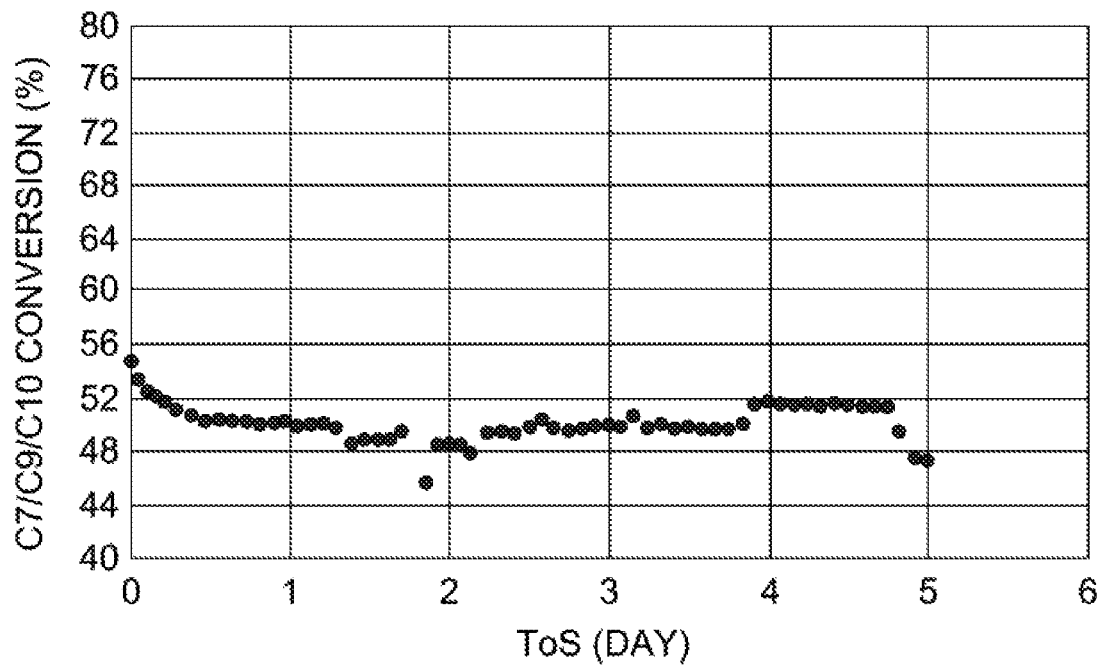
FIG. 8 shows $C_7$, $C_9$, and $C_{10}$ conversion for the transalkylation process of FIG. 7.

FIGS. 7-10 provide testing data for the catalysts reduced according to this Example 2, where the initial reduction was performed using a hydrogen treat gas that included 10 vppm CO. FIG. 7 shows the temperature profiles that was needed to maintain roughly constant conversion of toluene, $C_9$ aromatics, and $C_{10}$ aromatics (shown in FIG. 8). Similar to other figures showing reaction temperature profiles, in FIG. 7, solid data points represent inlet temperature, while hollowed circles represent average temperature. Again, the target amount of conversion was roughly 52%. As shown in FIG. 7, maintaining a roughly 52% conversion in FIG. 8 required an average bed temperature increase of roughly 60° F. (~33° C.) over the course of 5 days. This is in contrast to FIG. 2, where no temperature increase was required over the course of 10 days to maintain the target of roughly 52% conversion shown in FIG. 3.

Figure 9:
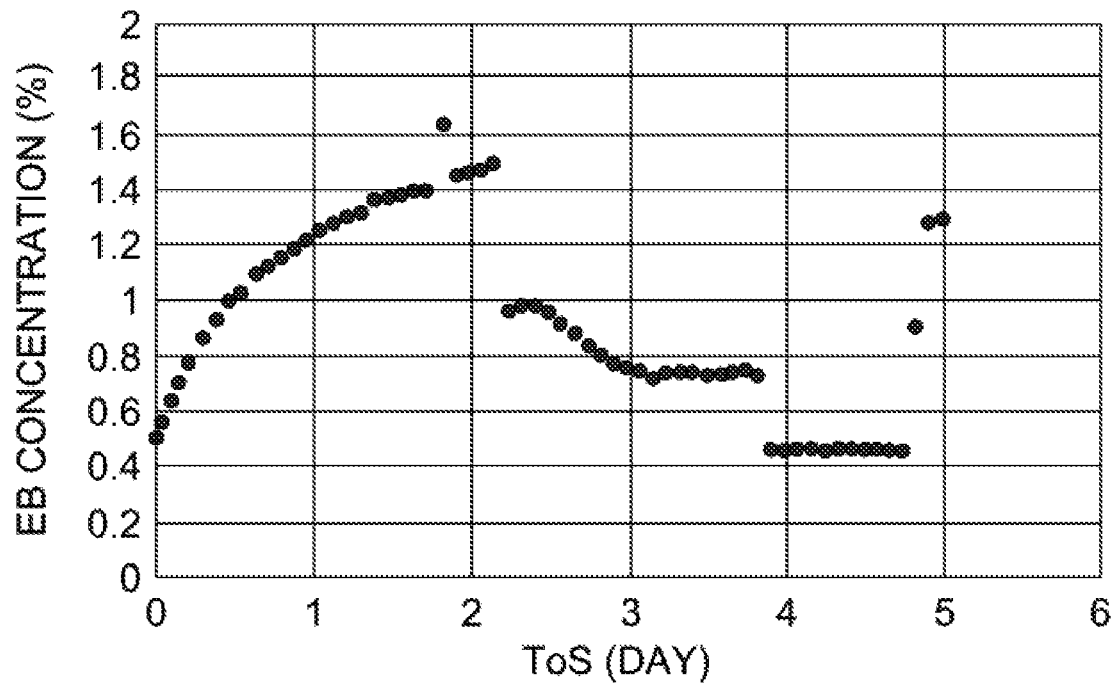
FIG. 9 shows ethylbenzene concentration for the transalkylation process shown in FIG. 7.

With regard to de-ethylation, FIG. 9 shows that removal of ethyl groups was significantly lower for the catalysts that were reduced in the presence of CO. Although the temperature was increased by roughly 40° C. during the 5 day testing period, the highest de-ethylation achieved was still below 90%. Additionally, during the initial period prior to the ramping of temperature, the conversion of de-ethylation dropped dramatically from around 85% to less than 60%.

Figure 10:
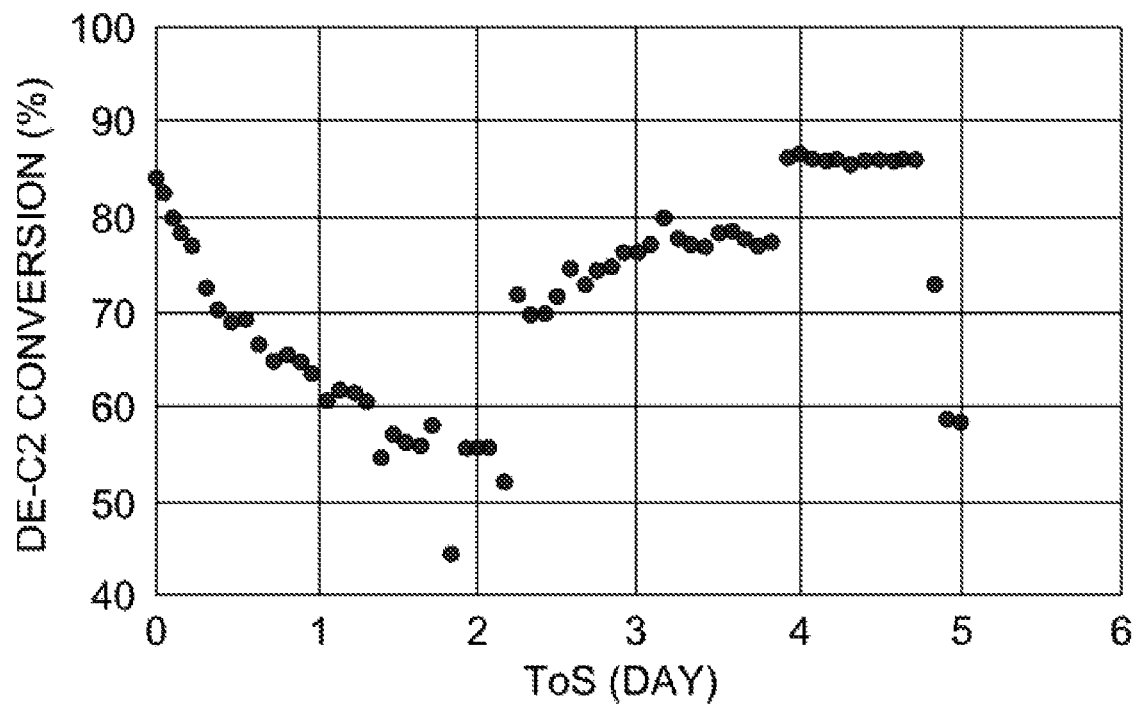
FIG. 10 shows de-ethylation conversion for the transalkylation process shown in FIG. 7.

FIG. 10 shows the ethylbenzene concentration in the products. Based on the relatively low levels of de-ethylation in FIG. 9, it is not surprising that increased amounts of ethylbenzene were observed in the products.

The overall result demonstrated by FIGS. 7-10 is that performing the initial reduction of a low metal content catalyst with CO present in the atmosphere at an appreciable concentration results in a catalyst that deactivates over time, even if the atmosphere during the subsequent transalkylation does not contain CO. By contrast, as shown in FIGS. 2-6, if the initial reduction is performed using a hydrogen-containing treat gas substantially free of CO, the low metal content catalyst maintains activity after exposure to oxygen, a second reduction step, and use of hydrogen-containing gas that includes CO during the transalkylation step.

Transalkylation Example 3—Reduction Followed by Short Oxygen Exposure

The third set of reducing conditions was used to reduce catalyst in a pilot unit. The third set of conditions included ambient pressure (~0.1 MPa-a) and a hydrogen-containing gas flow corresponding to 100% $H_2$ (such as electrolytic hydrogen). The catalyst sample was heated at a ramp rate of 60° F./hr (~33° C./hr) until a temperature of 350° C. was reached. The sample was then held at 350° C. for 2 hours. The sample was then cooled to ~20° C. while maintaining the 100% $H_2$ atmosphere.

After the reducing procedure, the catalyst was extracted from the pilot unit and exposed to static air for ~3 hrs. The catalyst was then exposed to a second reducing step according to the reducing conditions for Example 2, where the hydrogen treat gas included 10 vppm of CO. This was intended to represent the concept of performing ex-situ reduction in a first vessel, then transferring the catalyst to a reactor where a second reduction plus optional sulfidation is performed. After sulfidation, the catalyst was then exposed to the feed mixture under transalkylation conditions.

Figure 11:
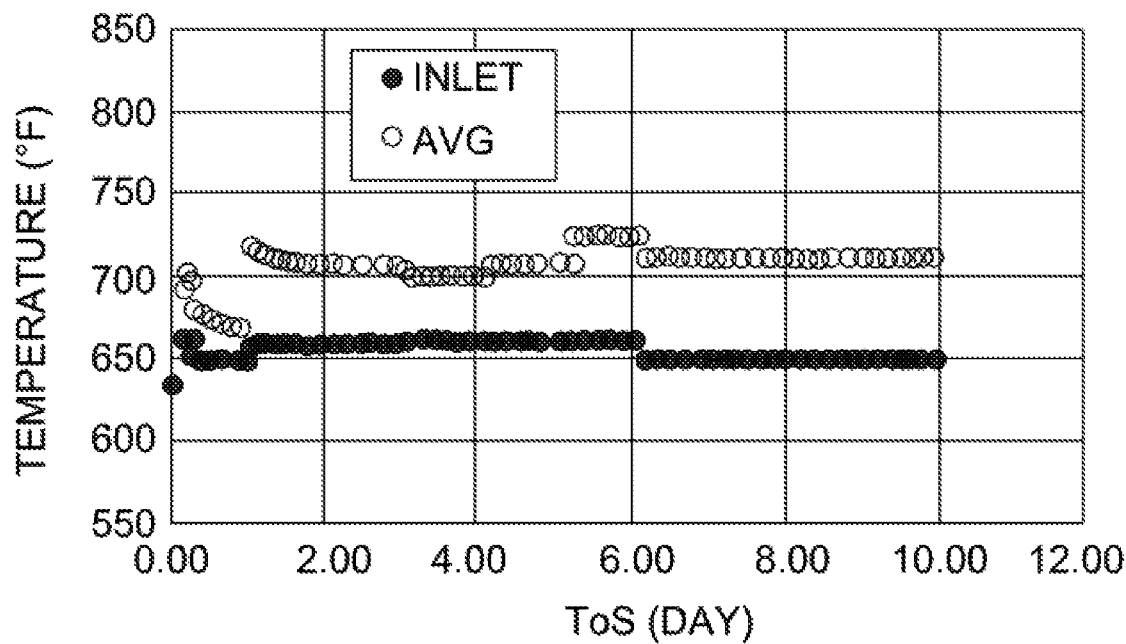
FIG. 11 shows temperatures associated with a third exemplary transalkylation process.
Figure 12:
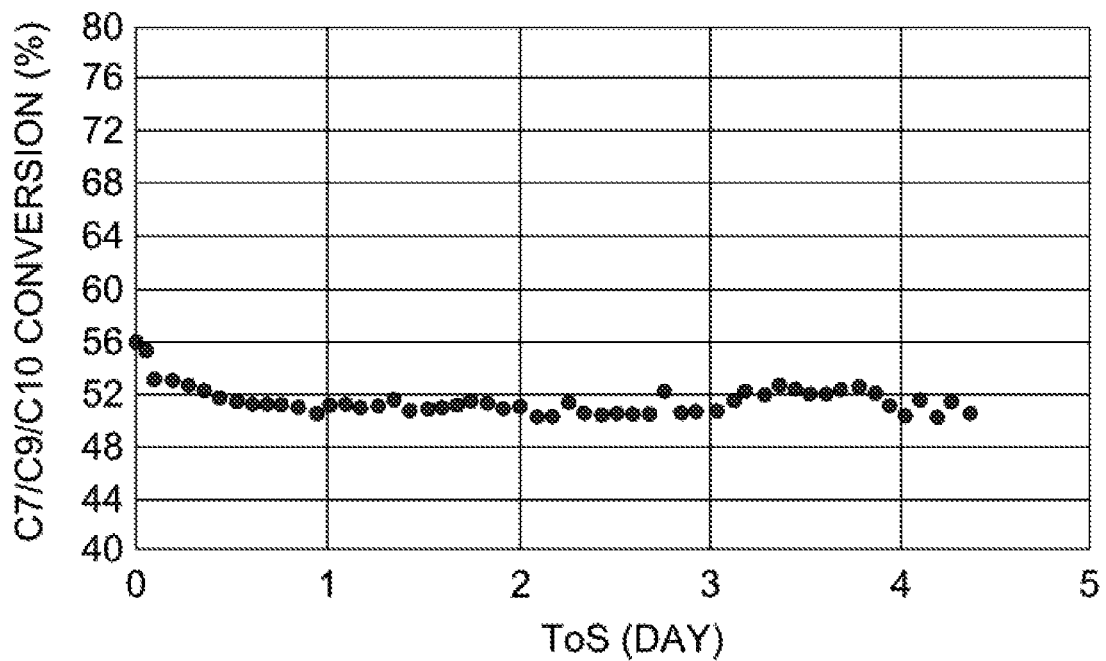
FIG. 12 shows $C_7$, $C_9$, and $C_{10}$ conversion for the transalkylation process of FIG. 11.
Figure 13:
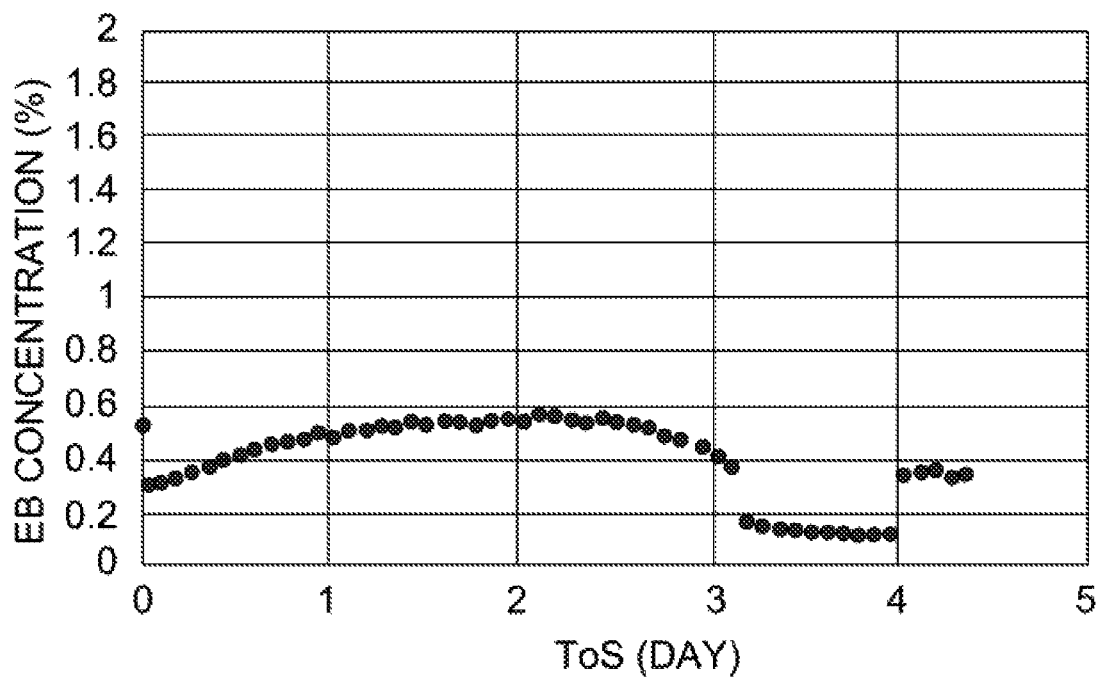
FIG. 13 shows ethylbenzene concentrations for the transalkylation process shown in FIG. 11.

FIGS. 11-14 show the results from the transalkylation. FIG. 11 shows the temperature profile that was used in an effort to maintain conversion of the $C_7$, $C_9$, and $C_{10}$ aromatics at 52% (FIG. 12). At that level of conversion, FIG. 13 shows that after a three day initial period, the catalyst was able to maintain greater than 90% de-ethylation at roughly the same temperature as the catalyst reduced under the baseline condition.

The results in FIG. 13 demonstrate several features. First, the activity of the catalyst after a reducing—oxidation—reducing sequence was not identical to the activity for a catalyst exposed to only the reducing conditions prior to startup. This indicates some impact on the catalyst activity from the oxygen exposure. However, performing the initial reduction (prior to oxygen exposure) using high purity hydrogen was sufficient to allow the catalyst to maintain desirable activity, even though the subsequent reduction was performed using hydrogen that included 10 vppm CO. This is in contrast to the catalyst from Example 2, where even a 33° C. increase in temperature was not sufficient to reach the desired level of activity for de-ethylation (see FIG. 9).

Figure 14:
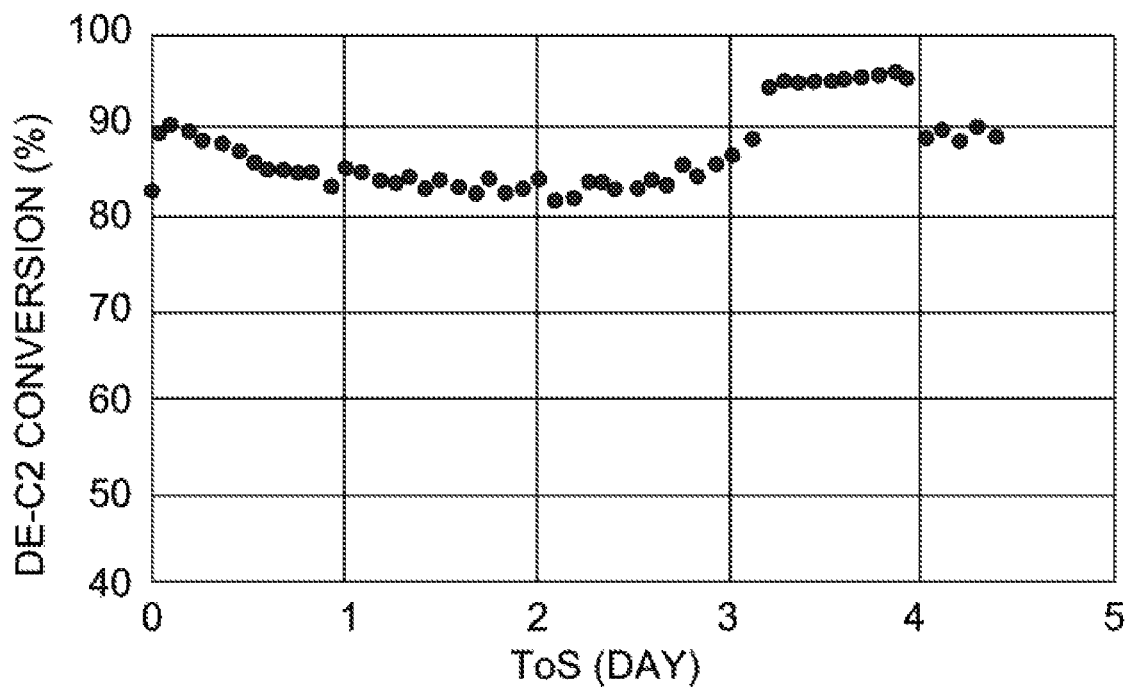
FIG. 14 shows de-ethylation conversion for the transalkylation process shown in FIG. 11.

Similarly, FIG. 14 shows that the catalyst exposed to oxygen for a short period of initial reduction was able to maintain a desired level of activity for removal of ethylbenzene from the products. This is in contrast to the results in FIG. 9, where the ethylbenzene concentration was greater than 0.4 even after increasing the transalkylation temperature.

Transalkylation Example 4—Extended Exposure to Oxygen after Reduction

The fourth set of reducing conditions was used in a laboratory scale reactor. The fourth set of reducing conditions were selected to represent reducing conditions that might be employed in a commercial setting for ex-situ reduction of catalyst, where a catalyst would be reduced ex-situ and then transported to a reactor site. It is noted that in both Example 3 and this Example 4, sulfiding is not performed until after the oxygen exposure.

The initial reduction step in the fourth set of conditions was performed at a pressure of ~0.1 MPa-a. The initial heating of the catalyst precursor sample under the fourth set of conditions was performed in an atmosphere corresponding to 100% $N_2$. The catalyst precursor sample was ramped at ~40° C./hr until a temperature of 275° C. was reached. A gas flow corresponding to 4 vol % $H_2$ in $N_2$ was then introduced into the reactor while the temperature was maintained at 275° C. for 1 hour. The resulting catalyst was then cooled to ~20° C. in a 100% $N_2$ atmosphere. After the reducing procedure, the catalyst was exposed to a forced air flow for 7 days.

After the air exposure, the procedure of Example 3 was followed to reduce then sulfide the catalyst. The catalyst was then exposed to the feed mixture under transalkylation conditions.

Figure 15:
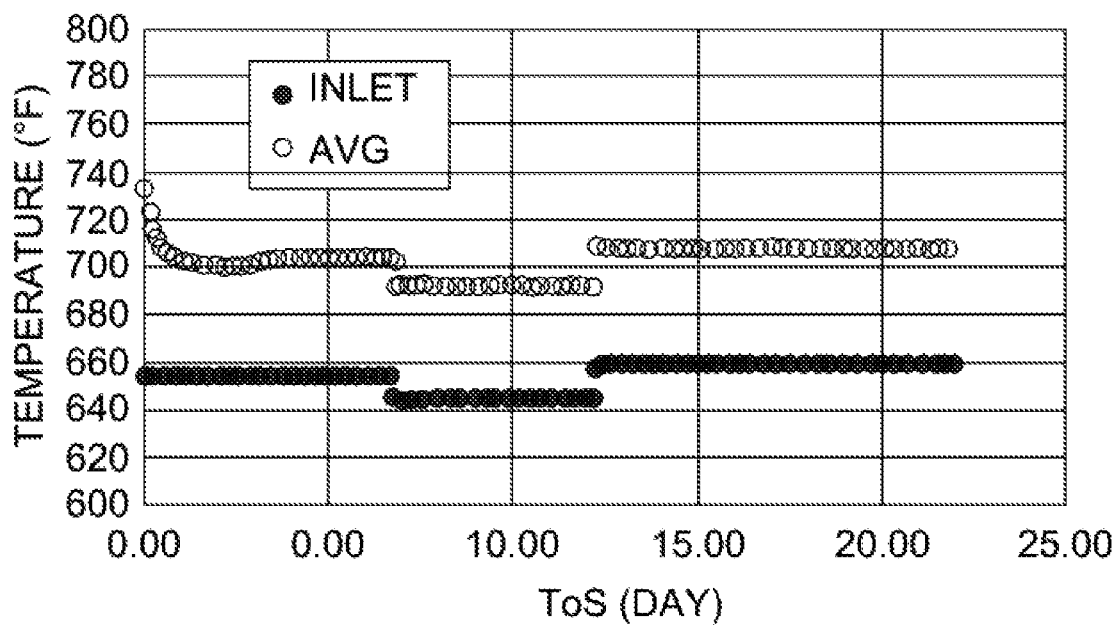
FIG. 15 shows temperatures associated with a fourth exemplary transalkylation process.
Figure 16:
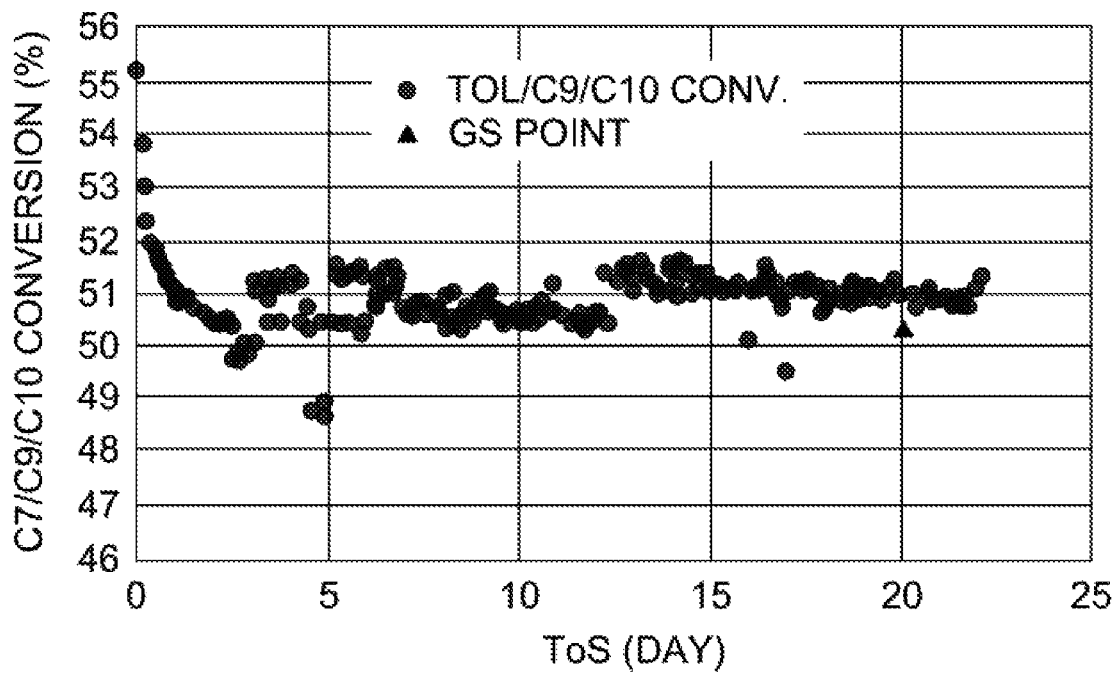
FIG. 16 shows $C_7$, $C_9$, and $C_{10}$ conversion for the transalkylation process of FIG. 15.
Figure 17:
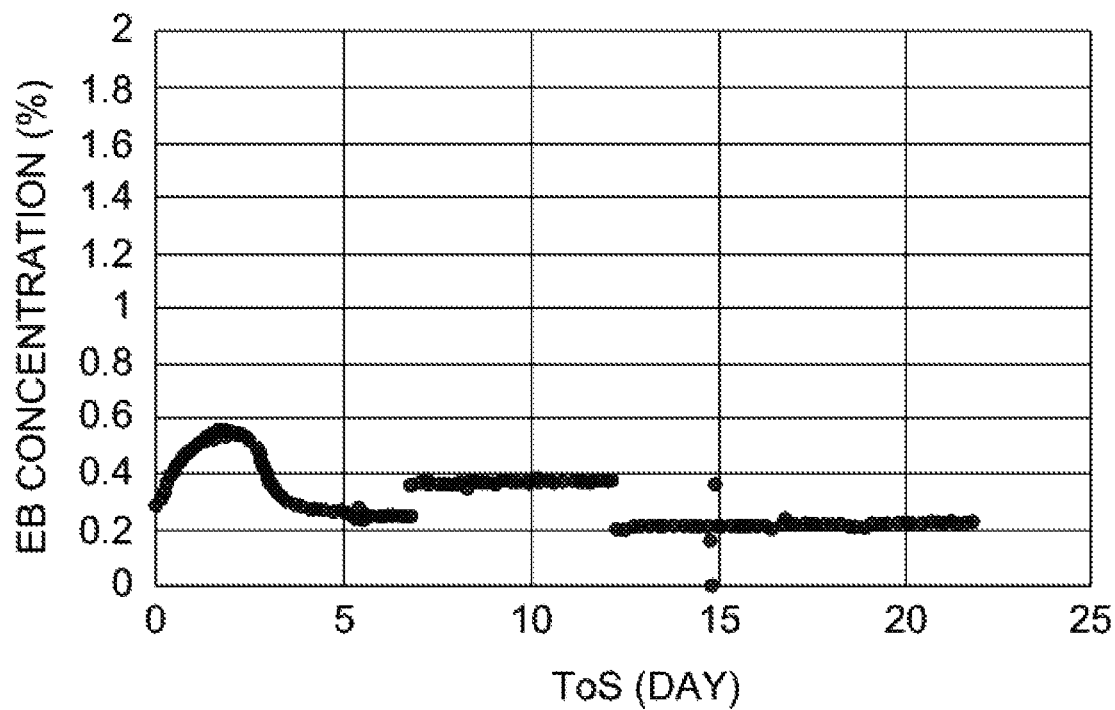
FIG. 17 shows ethylbenzene concentration for the transalkylation process shown in FIG. 15.
Figure 18:
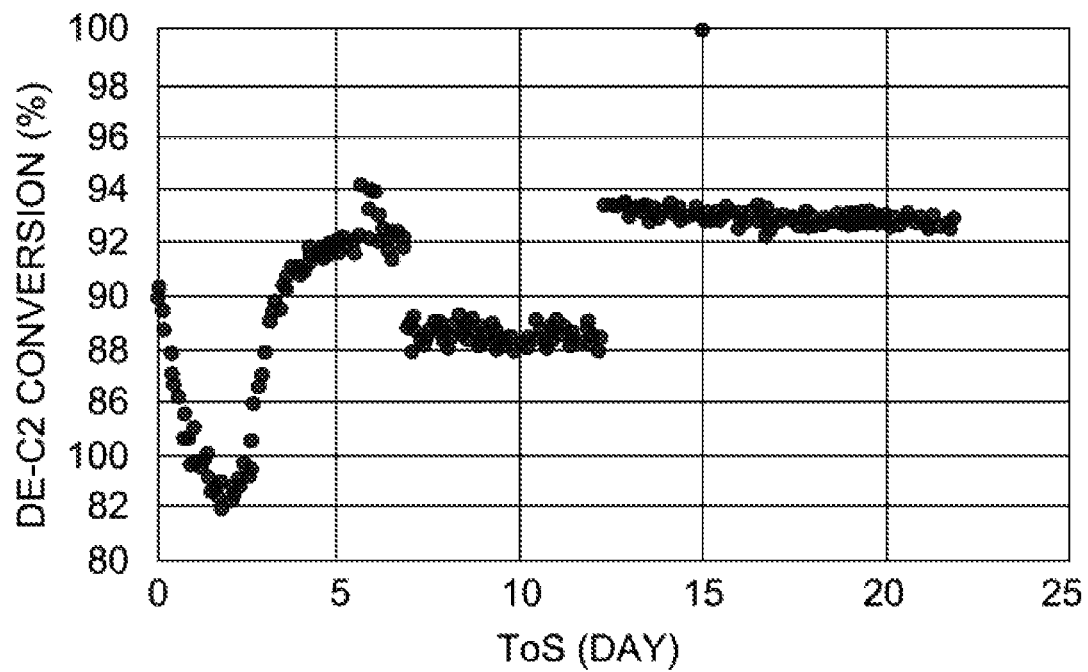
FIG. 18 shows de-ethylation conversion for the transalkylation process shown in FIG. 15.

FIGS. 15-18 show results from the transalkylation. FIG. 15 shows the temperature profile that was used to maintain a relatively stable level of conversion of $C_7$, $C_9$, and $C_{10}$ aromatics. A temperature similar to Examples 1 and 3 was used, but this resulted in 51% conversion of the $C_7$, $C_9$, and $C_{10}$ aromatics (FIG. 16), as compared with the 52% conversion from the other examples. Although the $C_7$, $C_9$, and $C_{10}$ aromatic conversion shown in FIG. 16 was slightly lower, the catalyst still had sufficient activity to maintain greater than 90% de-ethylation (FIG. 18). Additionally, after an initial startup period, the amount of ethylbenzene in the products was below 0.4 wt %, achieving target activity for ethylbenzene removal (FIG. 17).

The results in FIGS. 15-18 demonstrate that a low metal content catalyst can retain desirable activity even after extended exposure to oxygen after the initial reduction.

Xylene Isomerization Catalyst Example

Another type of potential low metal content catalyst is a xylene isomerization catalyst. The industrial xylene isomerization process involves two primary reactions—the conversion of ethyl benzene to benzene and ethylene, and the isomerization of xylene mixture to near equilibrium xylenes. Another important reaction is the hydrogenation of ethylene to ethane, usually aided by the metal function on the catalyst. Ethylene can alkylate aromatics, and therefore, is preferably converted to ethane instantaneously. Other side reactions include transalkylation, aromatic ring saturation and cracking leading to "xylene loss" and "ring loss".

In order to investigate the suitability of an ex-situ reduction procedure for a xylene isomerization catalyst, three types of catalyst startup procedures were used. A first procedure (Catalyst A) corresponded to ex-situ reduction, followed by exposure to oxygen. The second and third procedures (Catalysts B and C) were designed to represent in-situ reduction, either using a pure hydrogen treat gas or a treat gas including 10 vppm CO. The xylene isomerization catalyst corresponded to a stacked bed catalyst system that included two catalysts. The top catalyst bed included a catalyst comprising 0.03 wt % Pt supported on a zeolitic support. The bottom bed included a catalyst corresponding to 0.01 wt % Pt supported on a zeolitic support.

Catalyst A was exposed to a pre-reduction process, to represent ex-situ reduction of a low metal content catalyst. The pre-reduction process conditions included a pressure of ~0.1 MPa-a. The catalyst precursor sample was heated at a ramp rate of 90° F./hr (~50° C./hr) to reach a temperature of roughly 310° C., followed by holding at 310° C. for roughly 1.5 hours. The resulting catalyst was then cooled to roughly 20° C. The heating and cooling of the catalyst precursor/catalyst was performed using 100% $N_2$ as the gas flow, while a treat gas flow of 12% $H_2$ and 88% $N_2$ (substantially no CO) was used while the temperature was held at 310° C. for the 1.5 hours. The catalyst was then extracted from the reactor and exposed to static air for ~4 days.

To test xylene isomerization activity, the catalysts or catalyst precursors (including Catalyst A after pre-reduction) were each loaded into a pilot scale reactor and exposed to a startup procedure. The startup procedure began by pressurizing the reactor to 225 psig (1551 kilopascal, gauge pressure) with $H_2$. For Catalyst A and Catalyst C, this pressurization was performed using $H_2$ that included 10 vppm CO, while 100% $H_2$ was used for Catalyst B. $H_2$ was then flowed through the unit at 1.618 SCF per hour at ~20° C. for 1 hr, The reactor temperature was then increased by ~25° C./hr to reach a temperature of 200° C., followed by holding at 200° C. for roughly 16 hours. The reactor temperature was then increased by ~25° C./hr to reach a temperature of 360° C., followed by holding at 360° C. for roughly 4 hours. The reactor was then cooled to ~338° C. At this point, the feed for xylene isomerization was introduced. The inlet temperature was then slowly increased to achieve a target level of 75% ethylbenzene conversion. At this point, the hydrogen treat gases for Catalyst A and Catalyst C were switched to 100% $H_2$, to allow for comparison of xylene isomerization activities.

The conditions for the xylene isomerization reaction included a WHSV of 12 $hr^{-1}$; a reactor pressure of 225 psig (~1.6 MPa-g); a molar ratio of $H_2$ to hydrocarbons of 1.0; and a reactor inlet temperature of ~350° C. The amount of catalyst in the reactor corresponded to ~21 grams of xylene isomerization catalyst, loaded as whole extrudates mixed with an equal amount of inert diluent.

FIGS. 19-22 show the results from exposing Catalysts A, B, and C to the xylene isomerization feed under isomerization conditions. As noted above, the ethylbenzene conversion was maintained at roughly 75% during the test period shown in FIGS. 19-22.

Figure 19:
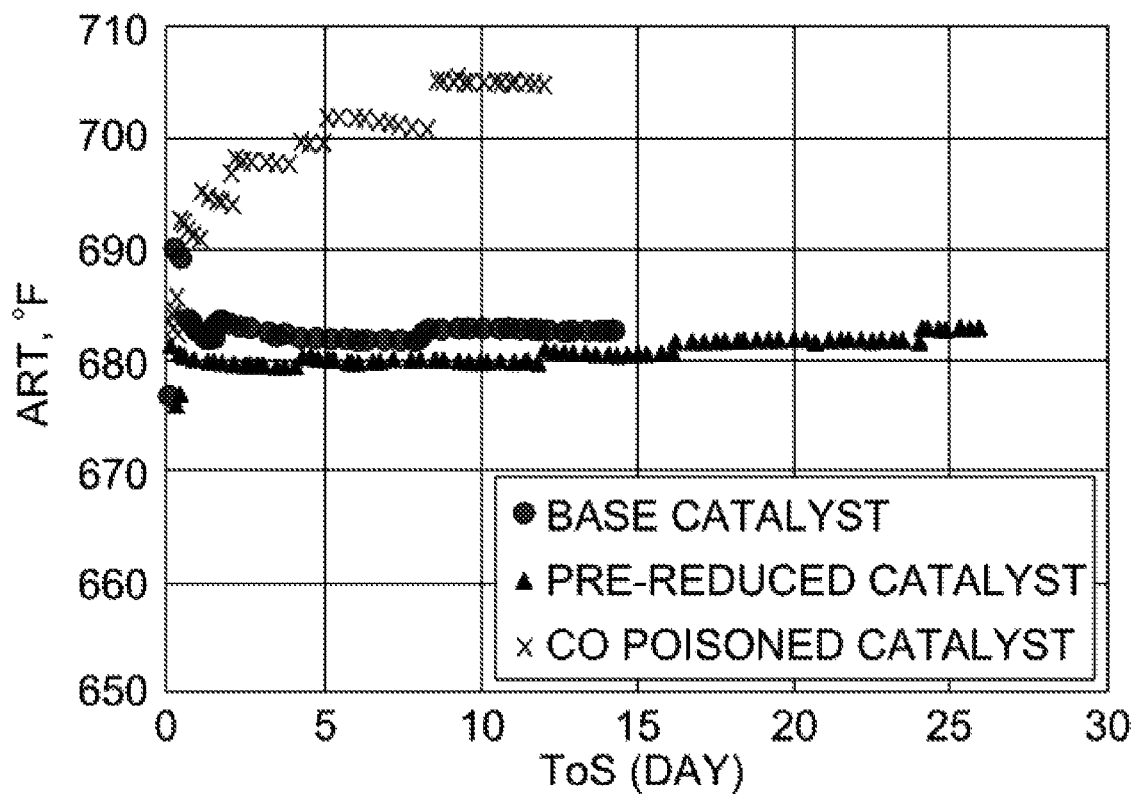
FIG. 19 shows average reactor temperature for three xylene isomerization processes utilizing three different isomerization catalysts activated using different methods.

FIG. 19 shows the average reactor temperature that was needed to maintain the ethylbenzene conversion at 75%. As shown in FIG. 19, Catalyst A ("PRE-REDUCED CATALYST") and Catalyst B ("BASE CATALYST") had similar temperature profiles. By contrast, Catalyst C ("CO-POISONED CATALYST") required substantial increases in temperature over time in order to maintain the desired level of conversion. Thus, even though Catalyst A and Catalyst C were exposed to similar reducing conditions that included 10 vppm CO, the pre-reduction of Catalyst A with high purity hydrogen allowed Catalyst A to maintain a desirable level of activity.

Figure 20:
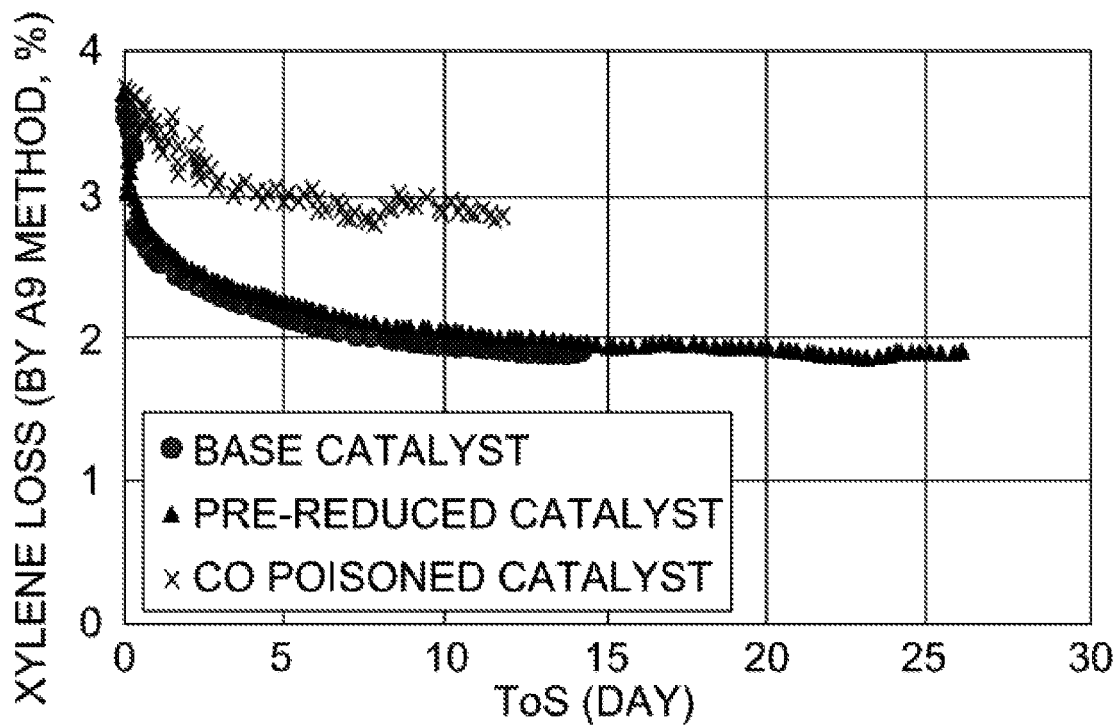
FIG. 20 shows xylene loss for the xylene isomerization processes shown in FIG. 19.

FIG. 20 shows the amount of xylenes lost due to aromatic saturation of xylenes. As shown in FIG. 20, Catalyst C resulted in an additional percentage point of xylene loss relative to Catalyst A or Catalyst B. Similar to FIG. 19, pre-reducing of Catalyst A allowed Catalyst A to maintain desirable performance for avoiding xylene loss, even though the in-situ reduction step included 10 vppm of CO.

Figure 21:
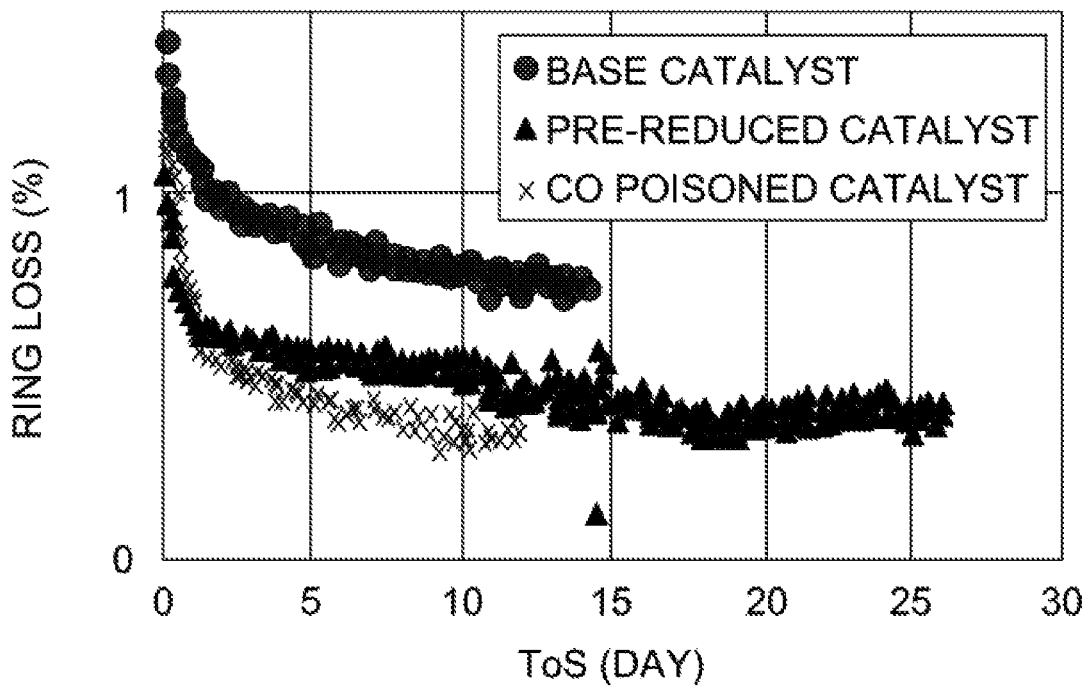
FIG. 21 shows ring loss for the xylene isomerization processes shown in FIG. 19.

FIG. 21 shows the amount of ring loss due to cracking of rings to aliphatic chains. FIG. 21 shows that the intermediate exposure to oxygen does have some impact on activity, as the ring loss for Catalyst A is more similar to Catalyst C than Catalyst B. In this case, however, Catalyst A and Catalyst C actually have preferably activity for avoiding ring loss in comparison with Catalyst B.

Although this disclosure has been described in terms of specific embodiments, it is not so limited. Suitable alterations/modifications for operation under specific conditions should be apparent to those skilled in the art. It is therefore intended that the following claims be interpreted as covering all such alterations/modifications as fall within the true spirit/scope of this disclosure.

What is claimed is:

1. A method for activating a catalyst, comprising:
   (I) providing a catalyst precursor comprising a hydrogenation metal and a molecular sieve, wherein the catalyst precursor comprises 0.5 wt % or less of the hydrogenation metal, based on the total weight of the catalyst precursor;
   (II) reducing the catalyst precursor in a first vessel in the presence of a first atmosphere comprising $H_2$ and 1.0 vppm or less of CO, based on the total volume of the first atmosphere, to form an activated catalyst;
   (III) transferring the activated catalyst to a second vessel; and
   (IV) treating the activated catalyst in the second vessel in the presence of a second atmosphere comprising $H_2$ and 3.0 vppm or more of CO, based on the total volume of the second atmosphere, to form a twice-activated catalyst.

2. The method of claim 1, wherein the method further comprises:
   (IIa) exposing at least a portion of the activated catalyst to a third atmosphere comprising 1.0 vol % or more $O_2$, based on the total volume of the third atmosphere, for an exposure time of 0.1 hours or more, to form an exposed activated catalyst, wherein the exposed activated catalyst is treated in step (IV) to form the twice-activated catalyst.

3. The method of claim 2, wherein step (IIa) is at least partially performed during step (III).

4. The method of claim 2, wherein the third atmosphere comprises air.

5. The method of claim 1, wherein the second atmosphere comprises 5.0 vppm or more of CO, based on the total volume of the second atmosphere.

6. The method of claim 1, wherein the second atmosphere comprises 10 vol % or more of CO, based on the total volume of the second atmosphere.

7. The method of claim 1, wherein the first atmosphere comprises at least 99 vol % of $H_2$, based on the total volume of the first atmosphere.

8. The method of claim 1, wherein the second atmosphere comprises at least 99 vol % of $H_2$, based on the total volume of the second atmosphere.

9. The method of claim 1, wherein the catalyst precursor comprises 0.1 wt % or less of the hydrogenation metal, based on the total weight of the catalyst precursor.

10. The method of claim 1, wherein the catalyst precursor comprises 0.05 wt % or less of the hydrogenation metal, based on the total weight of the catalyst precursor.

11. The method of claim 1, further comprising:
(V) sulfiding the twice-activated catalyst during or after step (IV).

12. The method of claim 1, wherein the twice-activated catalyst comprises a transalkylation catalyst or wherein the twice-activated catalyst comprises a xylene isomerization catalyst.

13. The method of claim 1, wherein the hydrogenation metal comprises at least one Group 8-10 noble metal.

14. The method of claim 1, wherein the hydrogenation metal comprises Pt.

15. The method of claim 14, wherein the catalyst precursor further comprises a second metal different from the first metal, the second metal comprising Sn, Ga, a metal that alloys with Pt, or a combination thereof.

16. The method of claim 1, wherein the hydrogenation metal is at least partly supported on the molecular sieve.

17. The method of claim 1, wherein the catalyst precursor further comprises a binder.

18. The method of claim 1, wherein the molecular sieve is a zeolite.

19. The method of claim 1, wherein the molecular sieve comprises one or more medium pore zeolites.

20. The method of claim 1, wherein step (I) comprises:
(Ia) providing at least a portion of the molecular sieve, at least a portion of the catalyst precursor, or a combination thereof;
(Ib) combining the at least a portion of the molecular sieve, the at least a portion of the catalyst precursor, or the combination thereof with a liquid dispersion of a compound of the hydrogenation metal to form a molecular sieve-metal mixture, a precursor-metal mixture, or a combination thereof;
(Ic) drying the molecular sieve-metal mixture, the precursor-metal mixture, or the combination thereof; and
(Id) calcining the dried molecular sieve-metal mixture, the dried precursor-metal mixture, or the combination thereof in an oxygen-containing atmosphere.

21. The method of claim 1, wherein the second vessel is a transalkylation reactor or a xylene isomerization reactor.

22. A method for activating a catalyst, comprising:
(I) providing a catalyst precursor comprising a hydrogenation metal and a molecular sieve, wherein the catalyst precursor comprises 0.05 wt % or less of the hydrogenation metal, based on the total weight of the catalyst precursor;
(II) reducing the catalyst precursor in a first vessel in the presence of a first atmosphere comprising $H_2$ and 1.0 vppm or less of CO, based on the total volume of the first atmosphere, to form an activated catalyst; and
(III) transferring the activated catalyst to a second vessel.

23. The method of claim 22, further comprising:
(IV) treating the activated catalyst in the second vessel in the presence of a second atmosphere comprising $H_2$ and 3.0 vppm or more of CO, based on the total volume of the second atmosphere, to form a twice-activated catalyst.

24. The method of claim 23, wherein the method further comprises:
(IIa) exposing at least a portion of the activated catalyst to a third atmosphere comprising 1.0 vol % or more $O_2$, based on the total volume of the third atmosphere, for an exposure time of 0.1 hours or more, to form an exposed activated catalyst, wherein the exposed activated catalyst is treated in step (IV) to form the twice-activated catalyst.

* * * * *